(12) United States Patent
Chimenti et al.

(10) Patent No.: US 7,515,781 B2
(45) Date of Patent: Apr. 7, 2009

(54) FIBER OPTIC, STRAIN-TUNED, MATERIAL ALTERATION SENSOR

(75) Inventors: Robert J. Chimenti, Short Hills, NJ (US); Bruce N. Perry, Flemington, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 11/483,024

(22) Filed: Jul. 7, 2006

(65) Prior Publication Data
US 2007/0019898 A1 Jan. 25, 2007

Related U.S. Application Data

(60) Provisional application No. 60/702,046, filed on Jul. 22, 2005, provisional application No. 60/703,733, filed on Jul. 29, 2005.

(51) Int. Cl.
*G02B 6/00* (2006.01)
(52) U.S. Cl. .......................................... 385/12; 385/13

(58) Field of Classification Search ...................... None
See application file for complete search history.

(56) References Cited

U.S. PATENT DOCUMENTS

| | | | | |
|---|---|---|---|---|
| 6,144,026 A | * | 11/2000 | Udd et al. | 250/227.14 |
| 6,586,723 B2 | * | 7/2003 | Moran et al. | 250/227.16 |
| 6,621,957 B1 | * | 9/2003 | Sullivan et al. | 385/37 |
| 6,626,043 B1 | * | 9/2003 | Bailey et al. | 73/705 |
| 6,820,489 B2 | * | 11/2004 | Fernald et al. | 73/705 |
| 6,885,785 B2 | * | 4/2005 | Dunphy et al. | 385/12 |
| 7,047,816 B2 | * | 5/2006 | Jones et al. | 73/729.1 |
| 7,251,384 B2 | * | 7/2007 | da Silva Junior et al. | 385/13 |

* cited by examiner

*Primary Examiner*—Omar Rojas
(74) *Attorney, Agent, or Firm*—Paul E. Purwin

(57) ABSTRACT

The present invention includes a method and system of measuring alteration, alteration type, and alteration-causing species in process fluids and equipment and for controlling the process feeds and conditions to maximize the yields and equipment lifetime by minimizing the alteration. The invention includes an optical sensor comprising an optical fiber, a fiber grating written within the optical fiber, strain-tuned elements fixed to the optical fiber and an unaltered element, and an altered element fixed to the unaltered element.

27 Claims, 9 Drawing Sheets

Implementation of Metal Loss Corrosion Sensor

Type 1 Strained-Tuned Metal-Loss Corrosion Sensor

Implementation of Metal Loss Corrosion Sensor

Corrosion and Thermal Effects Determine Metal Loss- to- Optical Transducer Operation Calculated Strain on the Fiber to the Metal Loss Corrosion for Type 1 Sensors Calculated Sensitivity of Strain on the Fiber to the Metal Loss Corrosion for Type 1 Sensors

Type 2 Strain-Tuned Metal Loss Corrosion Sensor

Re-Entrant Support Element for Type 2 Sensors

Metal-Loss Sensors with Biconical Contoured Metal Loss Elements

Strain on Fiber for Constant Radius and Biconical Metal Loss Elements

FIBER OPTIC, STRAIN-TUNED, MATERIAL ALTERATION SENSOR

This application claims the benefit of U.S. Provisional applications 60/702,046 filed Jul. 22, 2005 and 60/703,733 filed Jul. 29, 2005.

BACKGROUND OF THE INVENTION

The present invention relates generally to a fiber optic sensor system for the detection of material alteration in single or multiple phase fluids. One example of the present invention relates to the detection of metal-loss corrosion in process equipment during the production and processing of petroleum and hydrocarbons.

SUMMARY OF THE INVENTION

The present invention is an optical sensor that can monitor the fluid medium and the surrounding material. The sensor includes an optical fiber, one or more in-fiber gratings, such as Bragg gratings, that are produced within the optical fiber, a first sensor element having properties that can be altered by the medium, called the altered element, a second sensor element whose same properties are unaltered by the medium, called the unaltered element, and which is fixed to the first element, and at least one strain-tuning element that connects the second element to the optical fiber. The altered, unaltered, and strain-tuning elements combine to exert a predominantly axial strain on the in-fiber grating. The alteration-producing strain on the grating is measured by the changes in its optical reflection spectrum using swept-wavelength laser light propagating down the fiber and reflected from the grating.

The present invention is generally applicable to the detection of the magnitude and rate of the alteration of the altered sensor element by the medium and environment in which the sensor is placed. It is generally applicable to the detection of material alteration by processes that alter the dimensions, strength, and thermal and mechanical properties of the altered sensor element material. Examples of such material alteration processes are: corrosion, erosion, absorption, deposition, solubilization, dissolution, reaction, or vaporization by constituents of the medium.

The determination of the magnitude and rates of alteration of the altered sensor material by the fluid have utility and value through the relationship between these measured parameters and the magnitude and rates of similarly fluid-produced alterations of materials of construction of equipment used to produce, transport, store, or process the fluid medium. In the case of application of the invention to the determination of metal-loss corrosion rates of the altered sensor element used in crude oil processing equipment, fabrication of the altered sensor element from the same alloy as the process equipment provides the process operator a means to estimate the equipment corrosion rate.

The present invention is also generally applicable to the determination of the alteration-producing species type present in the medium through the magnitude and rate of alteration of a species-selective sensor material, Quantitative measures of concentration can be obtain if the dependence of the rates of alteration of the selective materials are known as a function of the concentration of altering species, temperature, and flow rate. In the metal loss corrosion application, the corrosivity of a crude to a particular alloy can be determined using the alloy as the altered sensor element. Specific species, such as sulfur, naphthenic acids, and chlorides can be determined by using alloys that have known differences in their corrosion rates for these species.

The present invention also relates to the production, transfer, processing, and storage of petroleum fluids, (referred to as "process" or "processes"). It also relates to petroleum processes that operate under relatively harsh conditions of temperature and turbulent multiple phase flow. However, the inventive aspects of the invention are broadly applicable to other processes, fluids, flow regimes, and temperatures.

The system to measure alteration magnitudes and rates of the altered sensor element includes integrated alteration-to-optical transducer and detection subsystems. The detection subsystem includes an optical fiber in which one or more Bragg gratings are produced along the fiber's length. Strain and temperature changes at a grating location produced by the altered sensor element and process temperature will change the optical properties of the gratings. One example of a changed optical property is the wavelength at which maximum reflectivity of the grating occurs. Light propagating in the fiber will be selectively reflected at this wavelength. Measurement of this peak reflectivity wavelength can be related to the local temperature and strain at the grating, and changes in these wavelengths can be related to changes in the local temperature and strain. The use of a fiber Bragg grating as a strain and temperature sensor and the means to detect changes in the optical propagation characteristics of the grating with changes in temperature and strain are well known in the art. While the description of the invention is presented using a Bragg grating as an example, other in-fiber grating types such as long period gratings may also be employed. In this case, the light propagating in the fiber will experience spectrally narrow loss regions which can be detected and related to temperature and strain changes in the grating, as has been described in prior art. For the purpose of clearly describing the instant invention, the example of a Bragg grating and the backscattering of light at the Bragg wavelength will continue in this specification.

The alteration-to-optical transducer is an important feature of the instant invention. The transducer converts the alteration of the altered sensor element, to a strain or temperature change of the in-fiber grating. Three multi-functional elements, that comprise the transducer, are designed and fabricated, depending upon the application environment, such as temperature, pressure, and fluid species and flow, to meet sensitivity and lifetime requirements of the sensor for that application. The application-specific sensor, so designed and constructed, uses the difference between the process and sensor fabrication temperatures and the alteration of the altered element, in combination, to produce a continuously changing, substantially axial strain on the fiber as the alteration occurs; the changing strain being in the range determined by an initial pre-alteration axial strain on the fiber grating produced by the thermal response of the three transducer elements, that is preferably not greater than about 2% at the operating temperature, and a final axial strain, produced by the thermal response of the transducer elements after the maximum alteration has occurred, that is preferably near zero with the sensor at operating temperature Distributed measurements of the material alteration can be made by coupling an alteration-to-optical transducer to the fiber, at each axial location of a grating at which the amount of material alteration is to be determined. Depending upon the application, each of the functional elements of the transducer may be comprised of one or more materials and fabricated or processed at one or more temperatures.

The altered sensor element is in contact with the fluid medium. Its function is to be altered in the fluid process in response to the same alteration process species and with the same, or relatable, alteration rates as that of the process equipment. An additional function of the altered element is to cause changes in the stress state of the other sensor elements in relation to the alteration that occurs.

The unaltered sensor element is also exposed to, but does not corrode, in the process fluid. An additional function of the non-corroding element is to form the entirety, or a part of, a continuous enclosure to prevent the fiber and strain-tuning elements from contact with the process fluid.

The strain-tuning, or re-entrant support elements, are enclosed within and attached to, said unaltered element and serves, in part, to support the fiber. Two of the elements support the fiber, one at each end of the grating. The strain-tuning elements serve the additional functions of transmitting the strain changes caused by the alteration process to the grating in the fiber and to bias or "tune" the strain changes to achieve the required sensitivity and operating life performance targets for the sensor. The tuning is automatically achieved by the temperature of the sensor and the materials and geometry of the re-entrant supports.

A sensor whose altered element has achieved maximum alteration is inactive as material alteration sensor; however this inactivity does not adversely affect the propagation of light through the fiber element. Therefore if the inactive sensor is one of a multiple array of sensors distributed on a single fiber, the remaining active sensors on the fiber can be used to continue to monitor the material alteration for which the sensors are designed.

Two classes of material alteration sensors are described in the present invention. For both classes, the unaltered element completely surrounds the fiber and the re-entrant fiber supports. The grating is approximately centered between the fiber supports, and the unaltered element is coaxial and concentric with the center of the grating. In one sensor class, Type I, the strain changes on the fiber, produced by material alteration, are predominantly axial. There is a single altered element for each sensor that is coaxial and concentric with, and completely surrounds, the unaltered and re-entrant support elements, and the fiber grating. The axial strain produced by any bending moments, caused by asymmetries in the fabrication or operation of Type 1 sensors, are negligible.

In the second sensor class, Type 2, there may be one or more altered elements at a single grating, each of whose longitudinal axis is not coincident with, but is parallel to and displaced from, those of the unaltered and re-entrant support elements and the fiber grating. The one or more altered elements may be attached to the surface of the unaltered element at one or more non-contiguous angular positions around the unaltered element. The Type 2 sensors impart axial strain on the grating through predominantly bending moments on the altered and unaltered sensor elements that are produced by the alteration process. In the case of a single altered element, the bending moment lies in the plane containing the parallel axes of the altered and unaltered sensor elements.

Both Type 1 and 2 sensors serve as material alteration sensors by the alteration of an altered sensor element material by the fluid medium to produce changes in the strain on the fiber as a function of the alteration process. Changes in the axial strain in the fiber cause a shift in the wavelength of maximum reflectivity of Bragg gratings through a change in the grating's periodicity and effective refractive index. A material alteration analyzer that consists of: one or more of the material alteration sensors distributed on a single fiber or on a multi-fiber array; an optical means to transfer the light propagating in each fiber in the array to the detection system; an optical detection system external to the fiber, comprising a suitable light source, preferably a laser or super-radiant diode, a wavelength determining element, and a detector to sense the wavelength shifts; a processor that receives the measured wavelength shifts along with temperature, grating location, and other process information and converts the measured shifts to material alteration magnitude and rates. The material alteration analyzer reports the magnitudes and rates along with other information to the process computer and control system that use this information to determine actionable options which depend upon the application. Key features of the present invention include: the operation of the sensor relies on a difference between the sensor fabrication and process operating temperatures, and alteration of the altered element; multiple sensors along a single fiber can be used to meet the sensitivity and operating life performance targets or provide redundancy for increased reliability; and sensors measuring different alteration processes and species, as well as temperature and vibration can be used on a single fiber.

In addition, for both Types 1 and 2 sensors, means are provided to protect the fiber from direct contact with the process fluid species and flow, thereby reducing the (a) rapidly varying transverse and longitudinal viscous drag and shear on the fiber produced in some processes by fluid flow and turbulent eddies leading to dynamic fatigue of the fiber; (b) damage to the fiber coating and generation of surface micro-cracks on the fiber caused by erosion from the impact of dispersed phase species that may be present in process or process fluid medium; (c) corrosion and stress-corrosion of the fiber surface by reaction with the fluid species; and (d) thermal gradients at the individual grating locations. The reduction of these effects serves to increase operating lifetime, and decrease flow-induced changes in the grating that lead to wavelength shifts in the reflected light that are unrelated to the alteration process and act as sources of noise.

The fiber protection structure is a structure that: (a) is the unaltered element, (b) provides support for deploying and attaching the sensor array to the process vessel or pipe, (c) is flexible in the choice of materials of construction, and mechanical functionality, (d) provides support for the fiber internal to its structure, (e) provides means to compensate for the thermal expansion differences and strains between the fiber and the materials of the sensor elements, (f) provides means to optimize the transmission of stresses caused by the alteration process to the fiber Bragg grating and to alter the strain sensitivity to the alteration process by the sensor geometry.

BRIEF DESCRIPTION OF THE DRAWINGS

FIG. 6(b) shows final strain state of the sensor in FIG. 6(a), where the sensor is at the process temperature and there is nearly complete metal-loss of the corroding element.

DETAILED DESCRIPTION OF THE PREFERRED EMBODIMENTS

EXAMPLE A

Metal-Loss Corrosion Sensor

Figure 1:
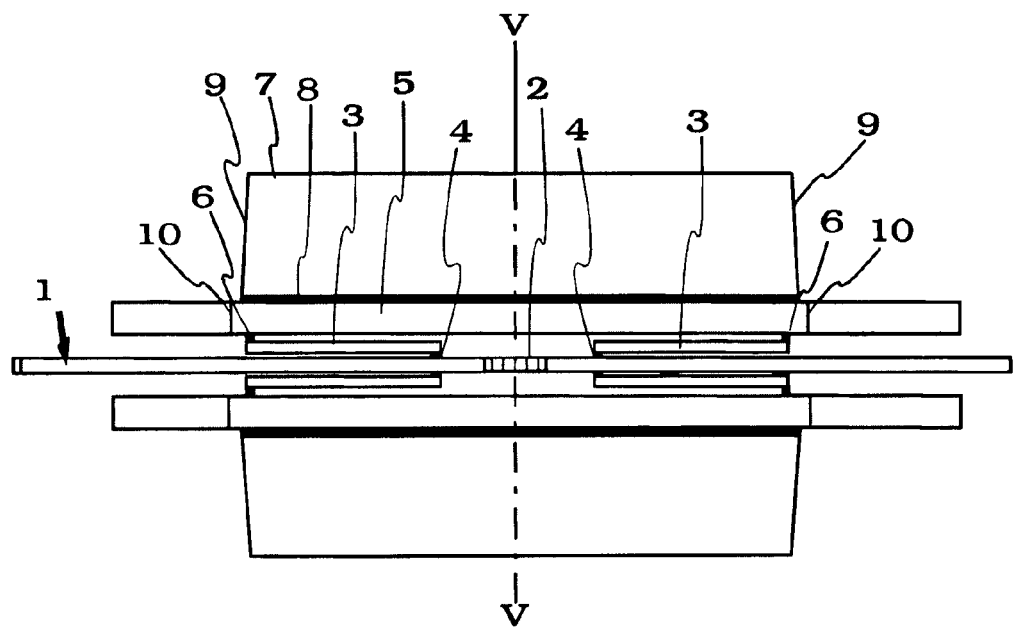
FIG. 1 shows the component elements for one embodiment of the Type 1 material alteration sensor of the present invention for metal loss corrosion as the alteration process.

In a preferred embodiment, the present invention includes a method and system for measuring corrosion metal-loss rates, corrosion type, and corrosive species in process equipment and for controlling the process feeds and conditions to maximize the yields and equipment lifetime, consistent with safe, reliable operation.

High performance, relatively low-cost corrosion sensing technology as in the instant invention would enable, for example, optimized utilization of corrosive crudes, and reductions in unplanned capacity loss, turnaround time, and inspection costs due to corrosion-induced equipment failures. Additional value is achievable with the application of the instant invention to corrosion monitoring of transfer, process, and storage equipment used for crude oil, fractions and derived products, and chemicals. Further value is achievable with the application to monitoring metal-loss corrosion in equipment used for the extraction and transport of crude oil from subsurface and sub sea deposits. Still additional value is achievable with the extension of the underlying concepts of the instant invention to other applications in petroleum fluids production, transfer and processing such as the detection of equipment fouling, material erosion, the presence specific chemical species in the fluid, and multi-phase flow.

In the corrosion example, current corrosion sensing technologies, for example electrical resistance probes, fall far short of the performance level required to achieve the economic incentives described above. Their shortcomings are that: measurements can be made only at a single location without moving the sensor, such operation posing considerable safety and environmental risks for many high temperature petroleum fluid processes; locations having the potential of enhanced corrosion, such as pipe elbows and bends, may not be accessible by current sensors; measurements at each location require an entry port through the transfer line, process unit, or storage vessel; a single sensor may not achieve the simultaneous process monitoring and economic requirements for sensitivity and operational lifetime; and the corrosion type and metal-loss rates measured by the sensors may not be representative of those that occur within the fluid boundary layer of the equipment wall that ultimately cause equipment failure. Consequently, while utilized because of the lack of competing technology, current corrosion sensing technologies are regarded as neither reliable nor accurate.

The above-mentioned shortcomings and limitations may be overcome by the present invention.

For both Types 1 and 2 sensor measurement of long term metal-loss corrosion rates, the corroding element is preferably fabricated of the same material as that of the process equipment for which a measure of the corrosion metal-loss rate is sought. For example, the corroding element may be plain carbon or 5% Cr steel for crude oil processes. The use of the process equipment alloy for the material of fabrication of the corroding transducer element increases the reliability of a metal-loss measurement. The measurement will better represent the corrosion metal-loss of the process equipment, if the metal alloys of the corroding sensor element and process equipment are the same or have similar metal-loss corrosion response to the corrosive species in the process fluid placed in the same temperature and flow environment.

Alternatively, there are applications of metal-loss corrosion measurements where it may be preferable to use metal alloys other than that of the process equipment. If, as one example, the objective of the measurement is to differentiate between the types of corrosion or to determine the principal corrosive species in the fluid, such as sulfides, naphthenic acids, or chlorides in the case of crude oil processes, then metals can be chosen that corrode selectively when exposed to these species. If the metal-loss rate can be calibrated or otherwise be related to the weight or volume % of the corrosive species in the process unit, then the sensor can be used as a fluid corrosivity sensor.

If the objective of the measurement is to sensitively detect the early onset of corrosion, a metal having a greater metal-loss rate than that of the process equipment can be used for the transducer corroding element. It can be recognized that the objectives of multiple applications may be achieved by the use of multiple sensors on a single fiber or fiber array, using for each sensor a different material for the corroding transducer element.

A preferred embodiment of the component parts of the Type 1 sensor used for corrosion in a high temperature, multiple phase petroleum process fluid flow are shown, in cross-section, in FIG. 1. The corrosion sensor comprises a corroding first material element tube (7) that corrodes in the process stream. The first material element being preferably the alloy of the process vessel or pipe, an example being a 5% Cr or carbon steel. The minimum wall thickness of the corroding element tube is determined by the metal-loss rate for the specific alloy in the specific fluid and fluid environment, and by the required operational lifetime and sensitivity of the sensor. An optical fiber (1), in which a Bragg grating (2) is written, is enclosed in a non-corroding second material element tube (5). Given the selected alloy for the corroding element, the non-corroding material is determined from two principal considerations. Firstly, the material should be substantially non-corrosive in the process stream and temperature for the required operational lifetime of the sensor. Secondly, the thermal expansion of the non-corroding element material at the process temperature should preferably be smaller than that of the corroding element. If the material is not sufficiently corrosion resistant to the degree demanded by the fluid corrosivity and the required operational lifetime, said material may be treated to improve its corrosion resistance, where application of a coating or cladding are examples.

As further shown in FIG. 1, the corroding element tube (7) is continuously attached (8) along its length to the non-corroding element tube (5) by means such as high temperature brazing, diffusion bonding, or by mechanically fitting such as by threading or thermally shrink interference fitting, or by any of these means in combination. The elements (5) and (7), so attached, form, and have the thermal expansion response of, a compound bi-metallic transducer element. The process operating temperature at which the sensor must operate must be considered in the selection of the attachment means. For example, if a high temperature braze or thermal shrink interference fit is to be used as said attachment means, the braze or shrink fit temperature must be chosen sufficiently higher than the process temperature to insure that the corroding and non-corroding elements remain as a compound element for the required operational lifetime of the sensor at the process temperature. For the case considered, where the coefficient of thermal expansion of the corroding sensor element exceeds that of the non-corroding element, the corroding element is in compression and the non-corroding element is in tension, when the assembled compound elements are taken up to the process temperature.

As further shown in FIG. 1, the fiber is supported by two re-entrant fiber support element tubes (3), placed symmetrically at each end of the grating such that their closest separation is e preferably no less than one grating length. The re-entrant element tubes are important to the invention in that they provide the means to change, or "tune" the strain state of the fiber in addition to supporting the fiber. The means are obtained by the way in which the re-entrant support element tubes are attached to the fiber and the non-corroding sensor element, and by the material properties and length of the re-entrant support tube elements.

As further shown in FIG. 1, each of the two re-entrant elements (3) is attached (4) to the fiber at or near their end nearest to the grating and to the non-corroding sensor element (5) at or near their opposite ends (6) by suitable attachment methods. Examples of said methods for circumferential attachment shown at (4) and at (6), as examples, are by glass solder and laser welding, respectively. Other examples include epoxy adhesive and mechanical threads, respectively.

Appropriate choices of material and length for the re-entrant support elements are dependent upon the material properties and lengths of the bi-metallic, compound corroding and non-corroding transducer, and fiber elements, and the process temperature. Said material and length choices are made so that the thermal expansion of re-entrant support elements compensate, to various degrees, the thermal expansion differences and strains between the fiber and the compound bimetallic transducer element at the operational process temperature and at various amounts of metal-loss due to corrosion. The material elements and the means to attach the optical fiber in the non-corroding material element are designed so that: a maximum substantially axial tensile strain on the fiber does not exceed approximately 2% at the process temperature prior to any corrosion metal-loss, and a minimum strain on the fiber is greater than and near zero at the process temperature after substantially complete corrosion metal-loss of the corroding transducer element.

The corrosion of the corroding material element changes the strain in the fiber, which causes a change in the wavelength of the light that is reflected from the Bragg grating. The wavelength shift is measured by a detection system and is reported as a corrosion metal-loss rate using a previously obtained calibration model.

As shown in FIG. 1, the ends (9) of the constant radius metal-loss element (7) are contoured (shown schematically as linear slopes) to efficiently transfer strain to the fiber, alter the strain sensitivity to metal-loss, substantially eliminate stress concentration at the leading edge of the metal-loss element inner-radius interface with the non-corroding element (5), and to minimize unwanted fluid circulation eddies at the outer radius leading edge of the metal-loss/fluid interface.

Figure 2:
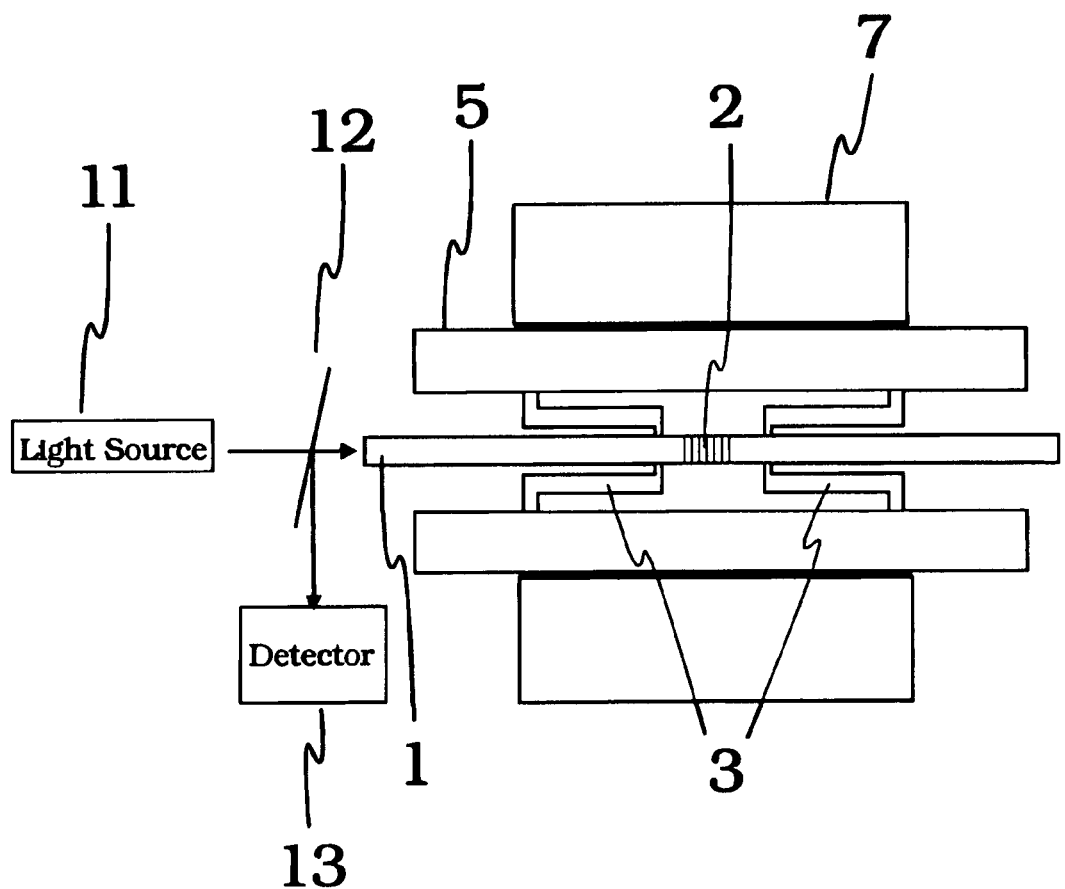
FIG. 2 shows the sensor of FIG. 1 on a single fiber along with the detection subsystem for the case where a Bragg grating is produced in the fiber.

As further shown in FIG. 1, the non-corroding element (5) may be optionally attached (10) outside of the sensor region, such as by laser welding, to an alternative fiber-protecting material for lower cost, structural integrity, flexibility using flexible armored cable, for example, or to the same or alternative material with greater wall thickness. The alternative material replaces the non-corroding transducer element between the sensors that are spatially-distributed along the fiber or fiber array, Multiple sensors can be fabricated along a single fiber, resulting in spatially distributed measurements requiring only 1 or 2 ports (the ends of the fiber) into the pipe. Sensors measuring different properties, such as temperature, corrosion type and corrosive species, fluid corrosivity, erosion, fluid-induced wall shear and vibration, may also be fabricated on the single fiber. FIG. 2 illustrates the operation of a metal-loss corrosion sensor showing the constant radius corroding (7) and non-corroding (5) elements, the fiber (1) and grating (2), and the re-entrant support elements (3). A light source (11), beam splitter or optical circulator (12), and detector (13) are shown to schematically indicate the 1-port or single-ended illumination of the fiber and measurement of the reflected light from the sensors.

It can be seen, in FIG. 1, that the sensor embodiment described is symmetric about the vertical plane that is normal to the fiber axis and passes through the center of the grating. The edge of the vertical plane, bisecting the transducer elements normal to the page, is shown as the line V-V in FIG. 1.

Figure 3:
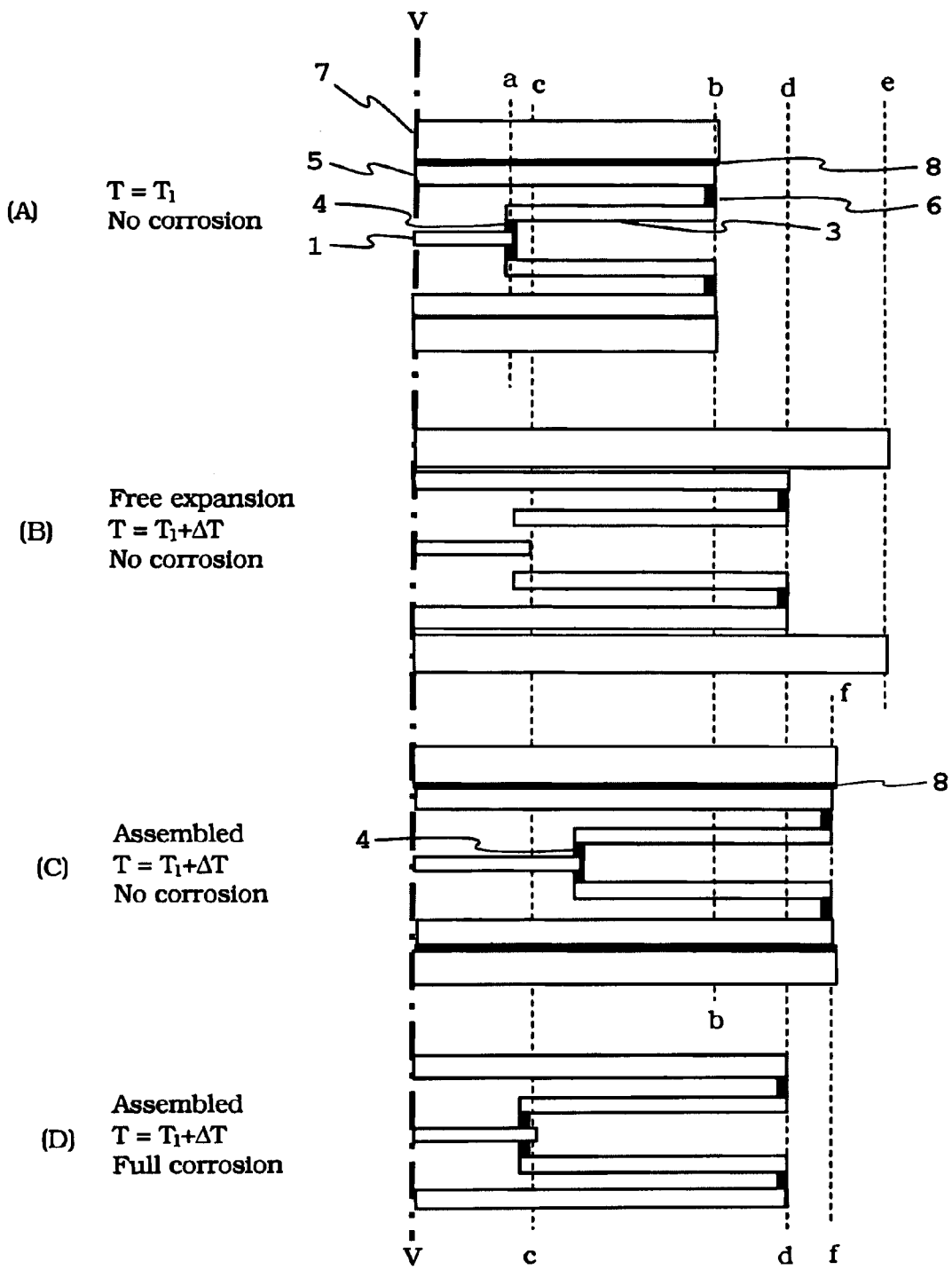
FIG. 3 shows the Type 1 sensor of FIG. 1 with expanded views of the right hand half of the sensor to explain the strain states of the component elements under different conditions of assembly, temperature, and of metal-loss of the corroding element. In the case shown, the coefficient of thermal expansion of the corroding element exceeds that of the non-corroding element.

FIG. 3 shows expanded views of the right-hand half of the constant radius metal-loss corrosion sensor of FIG. 1 in order to further explain its operation based upon corrosion metal-loss and thermal effects. The views in the four panels (A)-(D) schematically show a half of the sensor from the transverse symmetry plane V-V shown in FIG. 1 on the left to the end of the corroding and non-corroding transducer elements on the right. Not shown are the continuation of the non-corroding element and fiber past the end of the sensor and re-entrant support elements, respectively. Also not shown is the half-grating that is written in the fiber.

To describe the essential operational basis for the present invention, it is considered that the sensor elements, when assembled, are under no residual stress at an initial temperature, $T=T_1$.

FIG. 3(A) shows the section of the assembled sensor elements at temperature, $T_1$ where no corrosion has occurred. The corroding, non-corroding, re-entrant support tubes, and fiber elements, extending to positions labeled in the FIG. 1 as (7), (5), (3), and (1), respectively, are coaxial cylinders.

The metal-loss and non-corroding transducer elements, elements (7) and (7), respectively, are attached along their lengths, as previously described, thereby forming a compound, bi-metallic tube. Said attachment is indicated as (8) in FIG. 3. For this example, the case is chosen where the coefficient of thermal expansion of corroding element (7) exceeds that of the non-corroding element (5).

Still referring to FIG. 3, the re-entrant support element (3) is attached at its left end to the fiber or fiber coating surface (1) and at its right end to the non-corroding element (5). Said attachments are indicated as (4) and (6), respectively in FIG. 3(A). The re-entrant support element may be of a different material than the corroding and non-corroding elements (7) and (5), respectively. For this example, the coefficient of thermal expansion of the re-entrant support element (3) exceeds that of non-corroding element (5). The vertical dotted lines, labeled (a) and (b) in FIG. 3(A), indicate the initial axial positions of the right-hand ends of the fiber and metal elements, respectively. The element lengths are constrained, in this case, by the requirement of mutual assembly.

With reference to FIG. 3(B), the mechanical attachments between the two metallic elements (7) and (5), shown as (8) in panel (A), and between the support element (3) and the fiber (1), shown as (4) in panel (A), are considered severed and the sensor elements increased in temperature by amount, $\Delta T$, to the process operating temperature. Panel (B) shows the free expansion that occurs in the absence of any corrosion metal-loss, assuming that the left-hand ends of the corroding (7) and non-corroding elements (5), and the fiber (1) are attached to the V-V symmetry plane. The corroding and non-corroding elements, (7) and (5), respectively, elongate to the right from position (b) to (e) and (d), respectively. The re-entrant support element (3) is displaced to the right, since it remains attached, (6) to the non-corroding element (5), but elongates to the left due to the increase in temperature. The fiber (1) elongates to the right from position (a) to (c).

FIG. 3(C) shows the case when the elements (7) and (5) are mechanically attached (8), and the re-entrant support element (3), and fiber (1) are now mechanically attached (4) as described in panel (A) and the temperature raised from $T_1$ to $T_1+\Delta T$ as in panel (B). By virtue of the attachment of the elements, the corroding element (7) now extends from position (b) only to position (f). Element (7) cannot achieve its free expansion elongation to position (e) as in panel (B), since it is being constrained from doing so by a compressive force exerted by the other elements, although predominantly by the non-corroding element (5) due to its smaller coefficient of thermal expansion.

It can be further seen in FIG. 3(C), that the non-corroding element (5), extends from position (b), past its free expansion length at position (d) to position (f). This is the result of a tensile force exerted on element (5) by the other elements, although predominantly by corroding element (7), due to its greater coefficient of thermal expansion.

There is an additional force component, on the compound element, comprising elements (7) and (5) by virtue of their attachment, caused by the net thermal expansion of the fiber (1) to the right, from position (a) to position (c), and of the re-entrant support element (3) to the left, and the strain produced by the constraint that the re-entrant support element (3) is attached to the fiber (1) at its left end and to element (5) at its right end.

The displacements of the corroding (27), non-corroding (5), and combined fiber (1) and re-entrant support (3) elements from their free-expansion positions, shown in panel (B) to their actual assembled position at (f) in panel C, are due to the forces exerted on the elements that arise from the mutual mechanical attachments at elevated temperatures.

As the corroding transducer element (7) loses metal due to corrosion, the force component exerted by the corroding element (7) on the other elements diminishes and, in particular, the strain in the fiber (1) decreases. This decrease continues to occur with metal-loss corrosion until the corroding element (7) is completely corroded away. FIG. 3(D) shows this final strain case.

It can be seen in FIG. 3(D) that the fiber (1) is shown at position (c) which is its free-expansion position that is shown in panel (B). In this case, there is no strain on the fiber at the end point of the sensor's operating life. This is a special and preferred case where the thermal expansion of the re-entrant support element (3) is equal to the difference between the thermal expansion of the non-corroding transducer element (5) and that of the fiber and where there is no residual strain in the elements at $T_1$. A key feature of the instant invention is that the strain state of the fiber can be altered or "tuned", by selection of the material properties and length of the re-entrant support element given the lengths and properties of the other transducer elements.

A model has been developed to estimate the strain on the fiber for specific cases of sensor materials and properties, and corrosion metal-loss. Three examples are considered to illustrate the model results for strain and strain sensitivity to metal-loss as corrosion occurs. In all three examples the material for the metal-loss element (1) are the same. The sensor is fabricated so there is no residual strain on the sensor elements at $T_1=23°$ C. and the process temperature is $423°$ C. The corrosion metal-loss of the corroding element is considered to occur at uniform rate and in a direction normal to the cylindrical surface of the corroding transducer element. There is no bending moment on the transducer. The thickness of the corroding element is taken to be 1250 μm, which for these examples are determined by the expected metal-loss corrosion rates and the required operational lifetime of the sensor. Therefore when this amount of metal is reduced by corrosion, the corroding element is completely consumed and the sensor becomes inactive as a corrosion sensor. The length of the Bragg grating in the fiber is 1 cm.

Example 1

The material of the non-corroding element is a metal, such as 316 stainless steel. The stainless steel has a larger coefficient of thermal expansion than that of the metal of the corroding element. There is no re-entrant element in this example. Consequently, the length of the fiber is equal to that of the non-corroding element and is attached to each end of the non-corroding element Example 2

Example 2 is identical to Example 1 except the material of the non-corroding element is a low expansion glass-sealing alloy. The glass-sealing alloy has a smaller coefficient of thermal expansion than that of the metal of the corroding element.

Example 3

The material of the non-corroding element is the glass-sealing alloy, as in Example 2. Re-entrant fiber support tube elements of a high thermal expansion metal, such as 316 stainless steel, are employed. The supports are attached at their outer ends to the ends of the non-corroding element, and to the fiber at their inner ends. They are spaced by the fiber that contains the grating at the center of its span between the re-entrant support elements.

Figure 4:
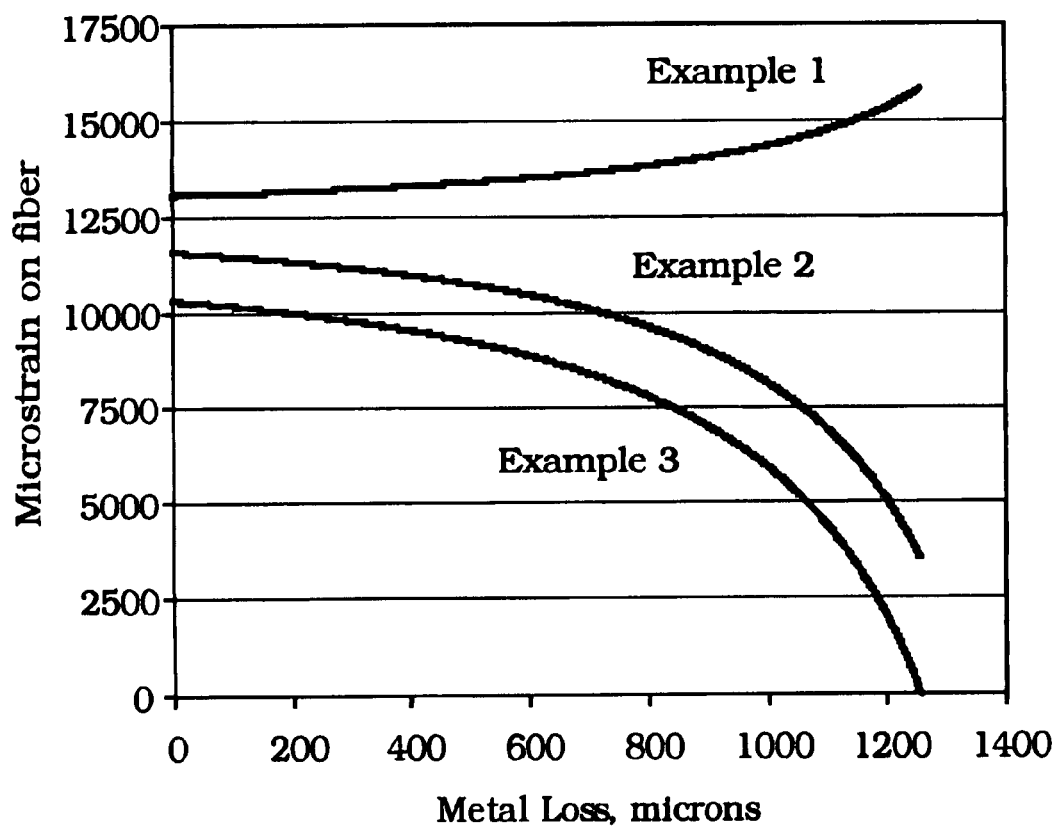
FIG. 4 shows the comparison of the calculated strain on the fiber for the Type 1 sensor shown in FIG. 3 for three examples.

FIG. 4 shows the results of the calculated strain on the fiber as a function of metal-loss for the three examples. In Examples 1 and 2, there are no re-entrant support elements. In Example 1, the non-corroding element material has a higher coefficient of thermal expansion than that of the metal-loss element. Therefore, when assembled as a compound element as raised to the $423°$ C. temperature of the Examples, the non-corroding element is in compression, being restrained from achieving its free thermally expanded length by the corroding element. However, the fiber is attached directly to the non-corroding element in these two cases and has a coefficient of thermal expansion considerably less than the two metal elements. Therefore the fiber is under tension. The value of the initial tensile strain sate on the fiber at zero metal-loss, can be seen in the FIG. 4 Example 1 curve as about 13000 microstrain. As corrosion removes metal from the corroding element, the portion of the force that compresses the non-corroding element diminishes and the non-corroding element expands towards its free expansion elongation. As the non-corroding element expands, the tension on the fiber increases from the initial strain state to nearly 16000 microstrain at 1250 microns of metal-loss.

In the FIG. 4 Example 2 curve, the non-corroding element has a lower coefficient of thermal expansion than the metal-loss element. Therefore, when assembled as a compound element and raised to the Example temperature, the non-corroding element is in tension, being elongated beyond its free thermally expanded by the corroding element. As discussed above, the fiber is initially under tension for this case as well. The value of the initial strain state on the fiber at zero metal-loss, is shown in the FIG. 4 Example 2 curve as about 11500 microstrain. In this case, however, as corrosion removes metal from the corroding element, the portion of the force that elongates the non-corroding element diminishes and the non-corroding element contracts toward its free expansion elongation. As the non-corroding element contracts, the tension on the fiber now decreases from the initial strain state to nearly 3500 microstrain at 1250 microns of metal-loss. This is clearly preferred over the Example 1 case, case since the strain reduction proceeds throughout the operational lifetime of the sensor and concomitantly reduces the probability of fiber and grating failure. It is preferable to design the sensor such that the initial axial tensile strain level on the fiber is below 2% and more preferable to be at 1.5% or less, and still more preferable to be at about 1% or less. It is also preferable to design the sensor such that the final axial tensile strain level on the fiber be preferably below 1000 microstrain and more preferable to be below 100 microstrain and still more preferable to be below 10 microstrain. The limited choices of materials and transducer dimensions result in the inability to achieve the simultaneous preferred initial and final tensile strains on the fiber. The use of a re-entrant fiber support element is an inventive step that provides the means for the strain behavior of the transducer elements on the fiber to be tuned so as to achieve the initial and final preferred strain levels.

This is illustrated in FIG. 4 Example 3. Example 3 adds the use of the re-entrant support elements to the sensor in Example 2. Example 3 uses the same lengths and the same materials for the corroding and non-corroding elements, respectively, of Example 2. However in Example 3, the fiber length is reduced from the length in Example 2. The fiber length is reduced by an amount that is greater than zero but no less than the length of the grating. Each end of the fiber is attached to a stainless steel support tube element whose length is one half of the difference between the length of the non-corroding element and the reduced length of the optical fiber and attached to the non-corroding element, as shown in FIGS. 1 and 3. The fiber is arranged so as to center the grating between the support elements. The calculated strain on the fiber as a function of corrosion metal-loss, using the re-entrant support elements, is shown in FIG. 4, Example 3. The figure shows that the re-entrant support elements provide the significant advantage of reducing both the initial and final strain states to 10300 and 24 microstrain, respectively.

Figure 5:
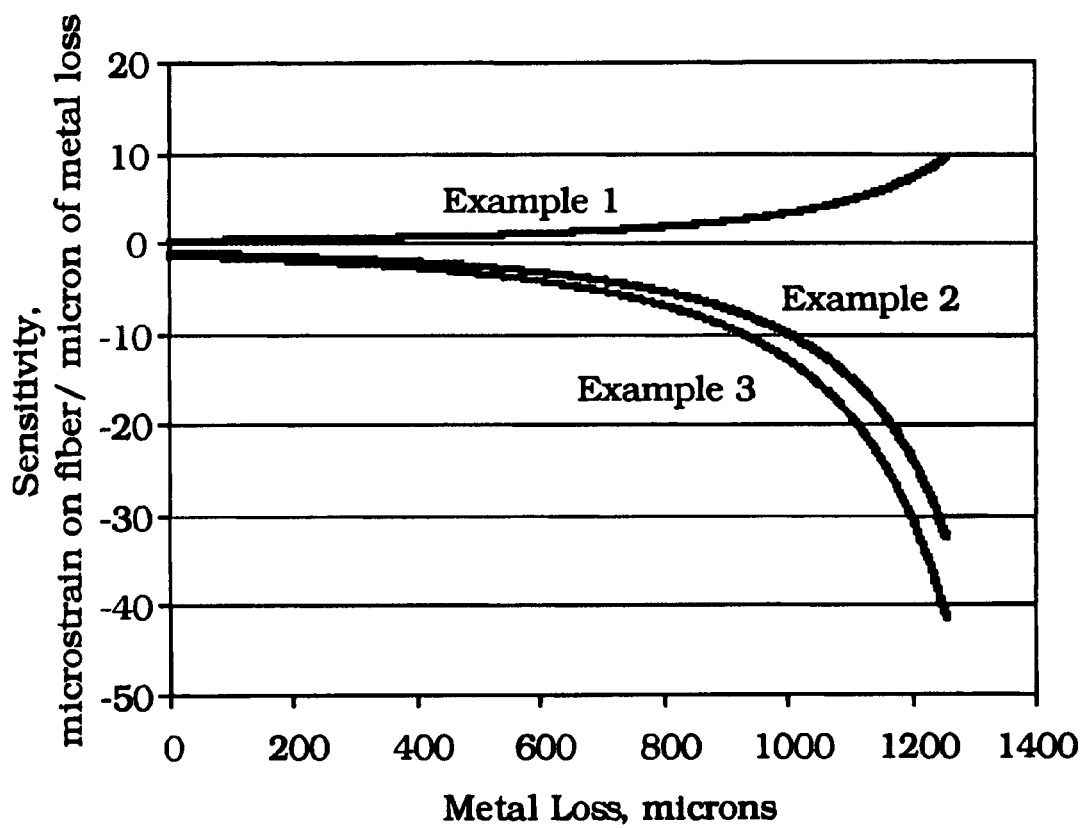
FIG. 5 shows the comparison of the calculation of the strain sensitivity to metal-loss as a function of metal-loss, for the examples shown in FIG. 4.

FIG. 5 shows the strain sensitivity, in units of microstrain per micron of metal-loss of the sensors, as a function of metal-loss, for the three Examples. It can be seen from the figure that the sensitivity of the Example 2 sensor is greater than that of the Example 1 sensor, (1.1 compared with 0.4 microstrain/micron metal-loss) even though the latter is under greater tensile strain throughout the corrosion process, as was shown in FIG. 4. A further benefit of the re-entrant, strain-tuned, support elements can be seen from the Example 3 curve in FIG. 5, which shows that while the strain level is significantly reduced from Example 2, as seen in FIG. 4 Example 2 and 3, the sensitivity to metal-loss is slightly improved to 1.36 microstrain/micron of metal-loss. FIG. 5 also shows that the lowest sensitivity (0.4 for Example 1), which for a grating with Bragg wavelength of 1550 nm, results in a wavelength shift greater than 0.15 pm, which can be measured under conditions of sufficient signal-to-noise. This corresponds to a 0.35 μm metal-loss sensitivity required by the application.

In Type 2 sensors, the axial strain in the fiber is produced primarily by a change in the curvature of the transducer elements, due to the interplay between the non-uniform thermal expansion of the assembled elements and corrosion metal-loss of the corroding element. The corroding element may be, for example, in the form of a one or more solid metal rods or rectangular bars, and the non-corroding element may be in the form of a single round or rectangular metal tube in which the fiber is supported by re-entrant support elements. The corroding element is attached, by means described for Type 1 sensors, to the surface of the non-corroding element at one or more angular positions around the circumference or perimeter of the non-corroding element.

For both Type 1 and 2 sensor configurations, enclosing the fiber sensor in the non-corroding metal tube has the significant advantage of protecting the fiber from the process fluid flow-induced micro-vibrations and erosion, and from process fluid species that may be deleterious to operating life of the fiber and fiber coatings.

The corroding and non-corroding transducer element materials are chosen to have different coefficients of thermal expansion. Consider that at some temperature, the assembled sensor will exert substantially no residual stress on the fiber and the axes of the corroding and non-corroding elements and fiber are parallel. When raised to the process temperature, the geometric asymmetry of the corroding and non-corroding transducer elements and the difference in their coefficients of thermal expansion will cause the sensor structure to bend. This puts an initial axial tension on the fiber prior to any corrosion metal-loss. As the corroding element loses metal, the non-corroding element straightens and the axial strain on the fiber is reduced.

Figure 6:
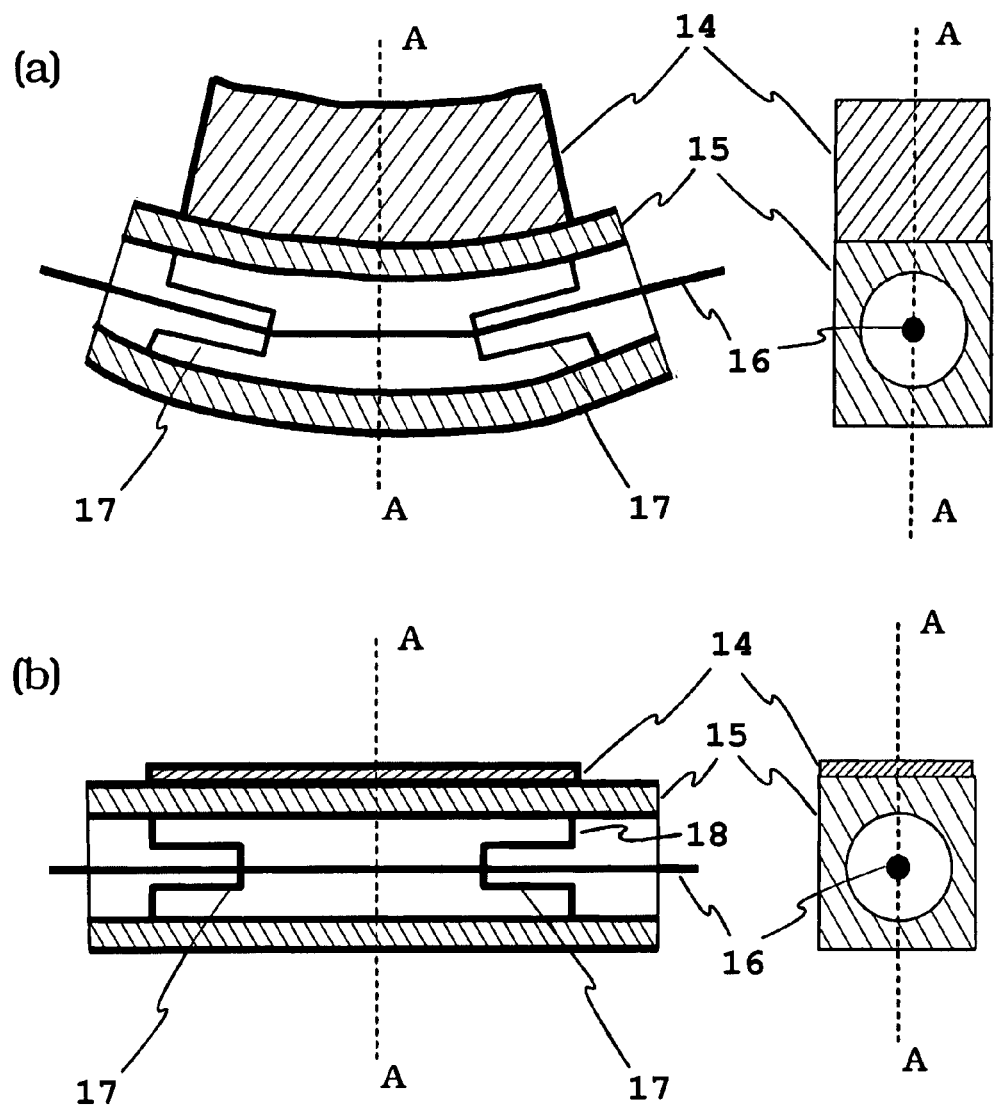
FIG. 6 (a) shows the side and end views of the components for one embodiment of a Type 2 material alteration sensor, as a corrosion sensor, for the initial strain state at process temperature and prior to metal-loss corrosion, the end view shown for the axial center of the device, indicated by A-A⁻.

FIG. 6(a) shows end and side views of one embodiment of a fiber Bragg grating sensor at process temperature comprising a single corroding metal bar element (14), mechanically attached to a non-corroding rectangular metal tube element (15), the latter containing a fiber (16) which contains a grating at A-A supported by re-entrant fiber supports (17). The longitudinal axis of the corroding element is initially parallel to, but displaced from the axes of the non-corroding element, re-entrant support tubes and fiber at some initial temperature and in the absence of corrosion. The initial strain-free case is not illustrated in the figure. When raised to the process temperature, a bending moment in the axial plane is produced due to the geometric asymmetry of the corroding and non-corroding transducer elements and the difference in their coefficients of thermal expansion. Consequently, the bending moment causes the sensor structure to bend, as shown in FIG. 6(a). For the case where non-corroding element (15) has a higher coefficient of thermal expansion than corroding element (14) and no corrosion metal-loss from corroding element (14) has yet occurred, the bend curvature is concave up, as shown. When the non-corroding element of the structure shown has a lower coefficient of thermal expansion than that of the corroding element, the structure will bend concave down. As the structure bends as shown in the figure, the fiber (16) will be slightly displaced vertically from the central longitudinal axis. This displacement is not shown in FIG. 6A.

FIG. 6(b) shows the nearly complete metal-loss from the corroding element (14). The elimination of the corroding element relaxes the bending moment on the non-corroding element (15), which then straightens, as shown.

Figure 7:
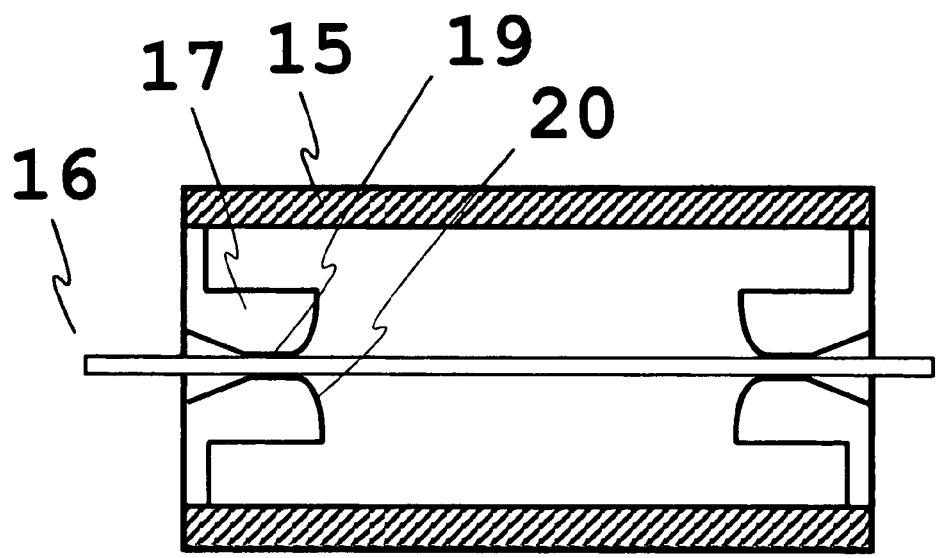
FIG. 7 shows an embodiment of a re-entrant support element for a Type 2 sensor.

The re-entrant support tubes, each attached at one of their ends (8) to the non-corroding element, are co-axial at temperature $T_1$. By virtue of their attachment to the non-corroding element, which bends when increased to temperature $T_1+\Delta T$, the re-entrant support tubes become rotated and are no longer coaxial with the fiber, as shown in FIG. 6(a). A tensile strain is produced on the fiber due to the outward rotation of the ends of the elements away from each other. After complete corrosion metal-loss of the corroding element occurs, the bending moment is removed and the re-entrant support tubes again become co-linear with the fiber as shown in FIG. 6(b). The tension due to the bending moment is also removed. FIG. 7 shows the sensor elements after corrosion of the corroding element. The non-corroding material, re-entrant support elements and fiber are labeled as (15), (17), and (16), respectively. The fiber is attached to the support tubes at (19). In order accommodate the angular mismatch between the axes of the re-entrant support elements and the fiber during at the process temperature during corrosion, the ends (20) of the support elements are contoured to a radius greater than or equal to the minimum bend radius of the fiber, given the sensor materials, dimensions, and operating temperature.

The corroding metal-loss element (7) of FIG. 1 has a constant radius. However, using a contoured rather than a constant radius metal-loss element can significantly enhance the performance characteristics of the sensor. The contour can be selected depending upon the performance characteristic of the sensor that is to be enhanced or improved.

Figure 8:
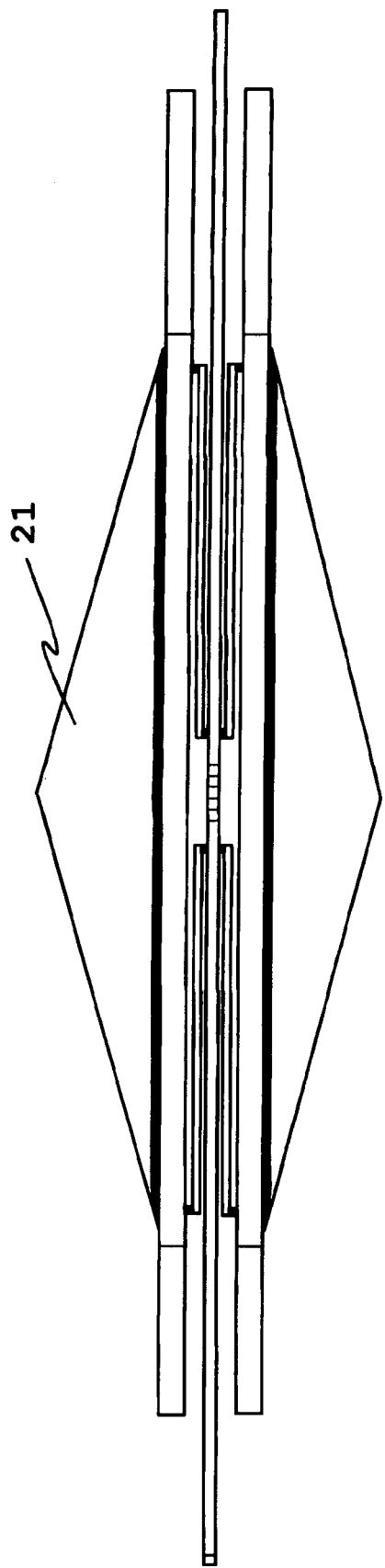
FIG. 8 shows an embodiment of a metal-loss sensor with a biconical contoured metal-loss element.

For example, FIG. 8 shows a metal-loss sensor with a biconical taper metal-loss element (21). All other sensor elements are the same as shown in FIG. 1 which has a constant radius metal loss element (7). Example 4 is considered in order to compare, quantitatively, the sensitivity of the biconical to the constant radius corroding metal-loss sensor. In Example 4, the maximum radius of the biconical element, prior to corrosion, is taken to the same as that of the constant radius element. The lengths and all of the other dimensions and properties of the metal-loss elements of the two sensor configurations are the same. Both configurations employ re-entrant fiber support elements. The slope of the constant radius element is zero, while that of each half of the biconical taper element is constant, and equal to the maximum height of the element divided by one-half of its overall length.

Figure 9:
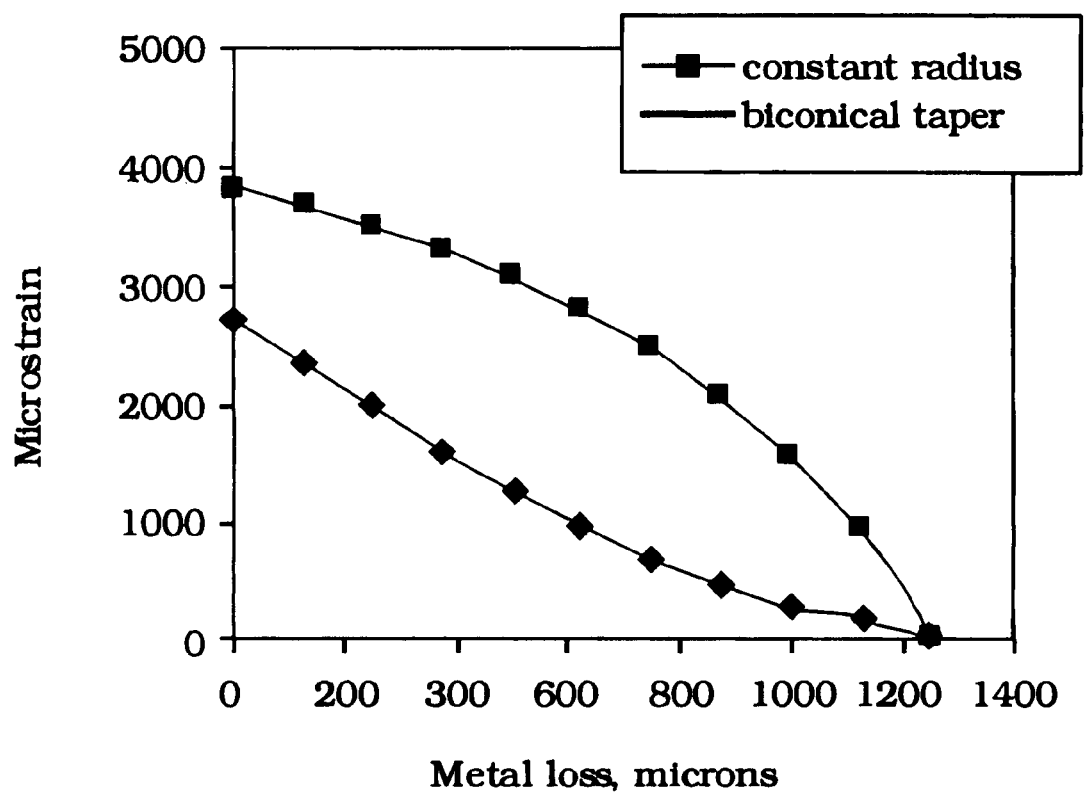
FIG. 9 shows a comparison of the strain on the fiber of metal-loss sensors having constant radius and a contoured, biconical metal-loss element.

FIG. 9 shows calculated strain for the two sensor configurations under the assumption that metal-loss occurs in a direction that is normal to the surface of the metal-loss element in each case. The strain value at zero metal-loss for the biconical configuration has an initial strain of about 30% lower than the constant radius case. However, the rate at which the strain changes with the amount of metal-loss for the bi-conical element at the early stages of corrosion exhibits more than a two-fold increase over the constant radius sensor, and is considerably more linear over the entire life of the sensor. The strain values at 1250 microns of metal-loss are both the same, since the metal-loss mechanism has removed the corroding metal-loss element in both cases.

EXAMPLE B

Erosion Sensor

A second example is a material alteration sensor where the alteration process is erosion by a dispersed solid phase material in the flowing fluid medium. The sensor embodiment can be very similar to that of the corrosion sensor, except that the material loss mechanism is the erosion of the altered sensor element by the impingement of the dispersed solid phase in the fluid. One property that differentiates the altered and unaltered sensor element materials for the corrosion sensor is the alloy composition that leads to the corrosion resistance to the fluid, while in the case of the erosion sensor one important property is the material hardness. The materials need not be restricted to metals, but can be ceramics, polymers or composites.

EXAMPLE C

Fouling Sensor

A third example is a material alteration sensor where the alteration process is the change in the thermal conductivity of an altered sensor element by the deposition of material onto the altered sensor element. Unlike the previous two examples, the measured shift in the Bragg grating reflectivity spectrum is due to a change in the temperature at the grating rather than a strain change as a result of the alteration of the thermal conductivity of the material of the altered sensor element. One application is the detection of fouling of fired furnace heater tubes. The tubes are externally heated and are convectively cooled by the process fluid flow internal to the tubes. Consequently, the tube metal temperature is determined, in part, by the heat transfer properties of the tube wall. Unwanted deposition of thermally degraded process fluid on the tube walls, commonly called fouling, will decrease the thermal transfer and the external surface of the tube will increase. This increase in temperature is local to the deposit that forms on the inside of the tube. A distributed array of fouling sensors can be used to determine both the onset and location of incipient fouling.

For the heater tube fouling application, as an example, the heater tube itself could serve as the altered sensor element and a small diameter capillary tube, in good thermal attachment to the heater tube wall and containing the fiber, serves as the unaltered sensor element. Since it is a temperature change, caused by the deposition of foulant, that results in the shift in the grating reflectivity spectrum (rather than the strain as in the previous examples), the re-entrant support tubes need only serve to support the fiber. A strain-bearing seal attachment between the fiber and one end of the re-entrant support element, required to detect a strain change, is not required for the detection of a temperature change.

EXAMPLE D

Moisture Sensor

A fourth example is a material alteration sensor where the alteration process is the change in strength of the altered sensor element due to the absorption or adsorption of one or more chemical species that comprise the fluid medium. An example of a chemical species is water in air. One application is the detection of the ingress of water under insulation covering heated pipelines. The altered sensor element could be a polymer, ceramic, or composite material that is selective to water vapor and whose structure changes reversibly with the adsorption or absorption of water having the effect of changing the strain that is produced on the fiber by the combined altered and unaltered sensor elements and the temperature at the sensor locations as described in the corrosion sensor example.

What is claimed is:

1. An optical sensor having a temperature $T_1$ placed in a medium having a temperature $T_2$ different from $T_1$, the optical sensor comprising:
    a) an optical fiber,
    b) a fiber grating within said optical fiber,
    c) a first element having a first coefficient of thermal expansion whose properties are altered by the medium, called the altered element, wherein said properties which are altered are material loss, material gain, chemical, thermal, and/or metallurgical,
    d) a second element having a second coefficient of thermal expansion different from said first coefficient of thermal expansion, called the unaltered element whose said properties are unaltered by the medium and fixed to said first element, and
    e) at least one strain-tuning element that is fixed to said second element and to said optical fiber wherein said optical fiber is not in contact with said first and second elements and wherein said strain-tuning element compensates for the difference between the thermal expansion coefficients of said first and second elements so that said optical fiber is under a tensile strain due to a difference in temperature between $T_1$ and $T_2$ so that the tensile strain of said optical fiber decreases as said first element is altered thereby causing reflected light from the optical fiber to change its wavelength.

2. The optical sensor of claim 1 wherein said first, second, and strain-tuning elements combine to exert a predominantly axial tensile strain on said optical fiber.

3. The optical sensor of claim 1 wherein said altered element is a corroding element that includes a material that corrodes in said medium.

4. The optical sensor of claim 1 wherein said unaltered element is a non-corroding element that includes material that does not corrode in said medium.

5. The optical sensor of claim 1 wherein first element is altered by the absorption of said medium.

6. The optical sensor of claim 1 wherein first element is altered by the reaction of said medium.

7. The optical sensor of claim 1 wherein first element is altered by the dissolution of said medium.

8. The optical sensor of claim 1 wherein first element is altered by the adsorption of said medium.

9. The optical sensor of claim 1 wherein first element is altered by the loss of material caused by said medium.

10. The sensor of claim 4 where said unaltered element is interposed between the said fiber and altered element.

11. The sensor of claim 4 wherein the altered and non-unaltered elements have a mutual interface and are fixed together at the entirety of their mutual interface so that their thermal expansion is mutually constrained.

12. The sensor of claim 11 wherein the said one or more strain-tuning elements are enclosed within the said unaltered element.

13. The sensor of claim 12 where at least one strain-tuning element supports the optical fiber-containing grating.

14. The sensor of claim 13 where two strain-tuning elements support the fiber-containing grating, one at each end of the grating.

15. The sensor of claim 13 where one or more of the strain-tuning elements have means to adjust the tensile axial strain on the fiber-containing grating.

16. The sensor of claim 15 where the one or more strain-tuning elements transmit changes in the strain on said fixed altered and unaltered elements to the fiber-containing grating.

17. The sensor of claim 16 where the sensor temperature and the alteration of the altered element, in combination, is a means for the strain-tuning elements to change the strain on the fiber-containing grating.

18. The sensor of claim 17 where the alteration of the altered element is a means for the strain-tuning elements to change the strain on the fiber-containing grating.

19. The sensor of claim 17 where the temperature of the sensor is a means for the strain-tuning elements to change the strain on the fiber-containing grating.

20. The sensor of claim 17 where the altered element completely surrounds the fiber and strain-tuning elements.

21. The sensor of claim 17 where the altered element is predominantly under compression and the unaltered element is predominantly under tension at the sensor operating temperature.

22. The sensor of claim 21 wherein said compression of the altered element diminishes as the alteration of the altered element occurs.

23. The sensor of claim 17 where the altered element does not completely surround the unaltered, fiber, and strain-tuning elements.

24. The sensor of claim 23 where the fixed altered and unaltered elements together produce a predominantly bending moment.

25. The sensor of claim 4 where the corroding element has a substantially constant radius prior to alteration.

26. The sensor of claim 4 where the altered element has a predominantly biconical taper prior to alteration.

27. The sensor of claim 1 where the grating is a Bragg grating.

* * * * *